United States Patent

Beyerlein et al.

[11] Patent Number: 4,503,166
[45] Date of Patent: Mar. 5, 1985

[54] CATION-REORDERED, BISMUTH-CONTAINING PEROVSKITES

[75] Inventors: Robert A. Beyerlein, Westfield; Kenneth R. Poeppelmeier, Flemington; Allan J. Jacobson, Princeton, all of N.J.

[73] Assignee: Exxon Research & Engineering Co., Florham Park, N.J.

[21] Appl. No.: 601,076

[22] Filed: Apr. 16, 1984

[51] Int. Cl.$^3$ .............................................. B01J 23/02
[52] U.S. Cl. ..................................... 502/303; 502/525
[58] Field of Search ............... 585/415, 417, 418, 520, 585/530, 533; 502/303, 525

[56] References Cited

U.S. PATENT DOCUMENTS

| | | | |
|---|---|---|---|
| 4,049,583 | 9/1977 | Lauder | 502/525 |
| 4,089,810 | 5/1978 | Diwell et al. | 502/303 |
| 4,107,163 | 8/1978 | Donohue | 502/303 |
| 4,110,258 | 8/1978 | Lauder | 502/525 |
| 4,134,852 | 1/1979 | Volin | 502/525 |
| 4,151,123 | 4/1979 | McCann | 502/525 |

FOREIGN PATENT DOCUMENTS 2155338 11/1971 Fed. Rep. of Germany ...... 502/303

Primary Examiner—Delbert E. Gantz
Assistant Examiner—A. Pal
Attorney, Agent, or Firm—Janet E. Hasak; Henry E. Naylor

[57] ABSTRACT

A class of cation-reordered, bismuth-containing compounds having a perovskite-type structure of the formula $$Ba_2La_yBi_{2-y}O_6$$

wherein y is greater than 0 but less than 1, is provided. Preferably, y is from 0.25 to 0.75, and most preferably y is 0.5.

The compositions herein are found to be particularly advantageous in the selective production of aromatic compounds from acyclic olefins, particularly in the production of benzene from propylene.

16 Claims, 4 Drawing Figures

CATION-REORDERED, BISMUTH-CONTAINING PEROVSKITES

BACKGROUND OF THE INVENTION

This invention relates to a class of cation-reordered, bismuth-containing compounds having a perovskite-type structure useful in oxidative dehydrogenation reactions and a process for their preparation. In addition, the invention relates to a process for selectively producing aromatic compounds from acyclic olefins, preferably propylene and isobutylene.

During a typical petroleum refining operation large quantities of low molecular weight paraffins and olefins are produced. Unlike paraffins which may be sold for fuels, olefins have undesirable combustion properties which hamper their potential use as fuels. Thus, much research effort has been directed to upgrading the olefins, either for use as fuel or as chemical intermediates in the chemical industry. For those olefins containing three and four carbon atoms much research has been directed toward obtaining reaction products such as dimer and aromatic products having greater potential commercial value, with bismuth oxide representing a conventional oxidation catalyst, particularly for producing dimers.

Oxidative conversions of unsaturated hydrocarbons have recently been conducted using various catalyst combinations. A recently published comprehensive review article on oxidative dehydrogenation of olefins is E. A. Mamedov, *Russ. Chem. Reviews*, 50, 291 (1981), which lists numerous references disclosing use of catalysts containing bismuth oxide in combination with other elements to convert olefins to dienes and aromatic products in the presence or absence of molecular oxygen.

SUMMARY OF THE INVENTION

In accordance with this invention a novel class of cation-reordered, bismuth-containing compounds having a perovskite-type structure of the formula:

$$Ba_2La_yBi_{2-y}O_6$$

wherein y is greater than 0 but less than 1 is provided. These compounds are further characterized by having the x-ray powder diffraction pattern as set forth in Table II hereof. Preferably, y is from 0.2 to 0.75, most preferably 0.5.

The above class of compounds may be prepared by heating a first precursor compound represented by the formula:

$$Ba_2La_yBi_{2-y}O_6$$

where y is defined above and which is characterized by having the x-ray diffraction pattern as set forth in Table I hereof, in the presence of an effective amount of oxygen at a temperature from about 600° C. to its melting temperature, for a sufficient period of time to produce a second precursor compound which is oxygen deficient and which has a perovskite-type structure and which is represented by the formula:

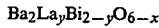

$$Ba_2La_yBi_{2-y}O_{6-x}$$

where y is as defined above and x is from about 0 to 1; and heating the second precursor compound to a temperature from about 400° C. to about 650° C. in an oxidizing environment.

The class of compounds herein, which are stable in air to at least 600° C., may be used in oxidative dehydrogenation reactions or in similar processes requiring solid oxidizing agents. In particular, the compounds herein are especially effective as catalysts in selectively producing aromatic products from $C_3$ and $C_4$ acyclic olefins, preferably benzene and xylene from propylene and isobutylene, respectively.

Specifically, most of the cation-reordered materials of this invention show nearly 100% selectivity for converting propylene to benzene at 510° C., as compared to a much lower selectivity observed when the first precursor compound described above, or the first precursor compound treated at high temperatures in flowing oxygen, is employed under identical conditions. Furthermore, the oxygen-deficient catalyst obtained after the propylene has been converted in accordance with the present invention can be regenerated by oxidation to yield a catalyst showing further improved performance in the conversion reaction.

DESCRIPTION OF THE PREFERRED EMBODIMENTS

Figure 1:
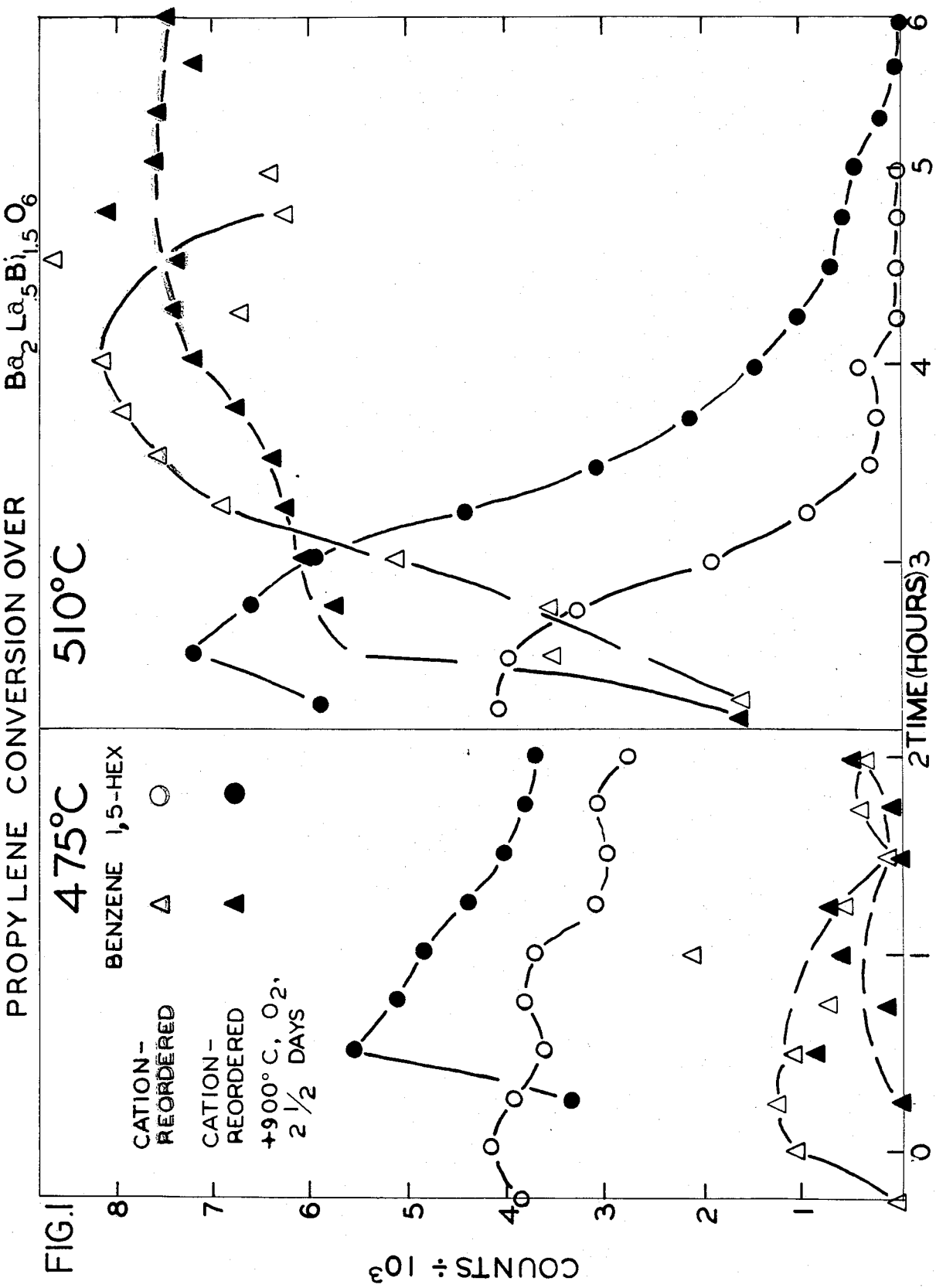
FIG. 1 is a graphical representation showing the relative amounts of 1,5 hexadiene and benzene produced from propylene (5% in helium) as a function of time at two different temperatures, 475° C. and 510° C., by use of two materials, (A and B) both of which are represented by the formula $Ba_2La_{0.5}Bi_{1.5}O_6$. Both are re-ordered but one (B) was obtained by treating (A) in flowing oxygen at 900° C. for 2.5 days prior to use.

The class of cation-reordered bismuth-containing compounds of the present invention are found by x-ray diffraction analysis to have the perovskite-type structure as described in A. F. Wells, Structural Inorganic Chemistry, Fourth Edition, Chapter 4, Clarendon Press (1975), and incorporated herein by reference.

The first precursor compounds, $Ba_2La_yBi_{2-y}O_6$, where y is greater than 0 but less than 1, used as starting materials to prepare the novel compounds herein, may be prepared by any convenient means known to those skilled in the art. For the investigations and experiments herein disclosed, they were obtained from a mixture containing barium nitrate, bismuth nitrate pentahydrate and lanthanum oxide. In this technique the nitrates and oxide in the appropriate amounts are oxidatively decomposed in air at 400° C. for 2 to 3 hours followed by successive regrinding and refining in air at temperatures of 800° to 900° C. for about 10 to 70 hours until no unreacted nitrate or lanthanum oxide can be detected in either the x-ray powder diffraction patterns or the infrared spectra of the oxygenated precursor compound product.

The x-ray pattern obtained for the conventional class of compounds $Ba_2La_yBi_{2-y}O_6$ thus obtained are shown in Table I for materials where y=0.25, 0.50, and 0.67. These patterns are typical of conventionally ordered $A_2BB'O_6$ pseudo-cubic perovskites. Here B is $La^{+3}$ and $Bi^{+3}$ and B' is $Bi^{+5}$. The appearance of certain ordering lines (hhh, h=2n+1) such as (111) and (333) is representative of such compounds. These same ordering lines are absent in the x-ray pattern of the novel compositions of the present invention as shown in Table II, indicating that cation reordering has occurred such that all B layers have the same stoichiometry. Thus, the compounds of the present invention have a different structure from the conventionally ordered $A_2BB'O_6$ structure.

The cation-reordered compounds of the present invention are prepared by heating the first (fully oxidized) precursor compound which is conventionally ordered and which can be prepared by any of the convenient methods previously described in the presence of an amount of oxygen effective for a particular temperature to obtain a second precursor compound which is an oxygen-deficient perovskite type structure of the formula $Ba_2La_yBi_{2-y}O_{6-x}$ where y is defined above and x is greater than 0 but no greater than 1. The amount of oxygen which is effective to produce the second precursor compound will depend primarily on the type of first precursor compound employed, the temperature at which the first precursor compound is heated, and the length of time for which the first precursor compound is heated. Typically, the heating will take place under a flow of a mixture of oxygen and an inert gas such as helium, or argon, at a flow rate of about 200 to 400 $cm^3$/minute. Higher or lower flow rates may be employed depending primarily on sample and reactor size.

The temperature at which the first precursor compound is heated is likewise dependent on many factors such as the type of first precursor compound and the amount of oxygen present. At minimum, the temperature should be about 600° C., but the temperature is preferably higher, for example about 600° C. to 1000° C. The time of heating will similarly depend on several factors such as the type of first precursor, temperature, and oxygen partial pressure. The interrelationships among the amount of oxygen employed, the temperature, and the type of first precursor compound can be expressed as follows: When the temperature is decreased, a lower oxygen pressure is required to obtain the product. As the content of lanthanum in the first precursor compound is increased, either the temperature must be increased or the oxygen partial pressure decreased and the time for heating must be increased to obtain the reduced product. Even when these parameters are adjusted, however, if y in the formula is increased beyond about 0.7 the second precursor obtained on cooling will generally not be a single-phase material but rather will comprise two phases which may be a mixture of the fully oxidized material (x=0) and the fully reduced material (x=1). If the first precursor compound is such that y is 0.5, when the compound is heated at between about 600° C. and 1000° C. the oxygen partial pressure will be between about 0.001 and 0.00001 atm, depending on the temperature. The preferred temperature range for heating is about 800° C. to 1000° C. and most preferred is about 900° C. to 1000° C. When a temperature of about 1000° C. is employed when y is 0.5, the oxygen partial pressure must be about 0.001 atm to obtain the second precursor compound, whereas if the temperature is about 950° C., the oxygen partial pressure is generally about 0.0001 atm and the time required is at least 8 hours, preferably 10 to 12 hours. When y is increased to 1, no oxygen-deficient precursor will be obtained unless the oxygen partial pressure is reduced or the temperature is increased.

The second precursor compound thus obtained is then oxidized to form the cation-reordered product by heating the compound at a temperature no greater than about 650° C. in an oxidizing environment, preferably at about 400° C. to 600° C., and more preferably 600° C. The time required for this oxidation will depend on the type of precursor employed, the temperature, the oxygen partial pressure, and the rate of gas flow, but is generally from about 1 to 4 hours, more preferably from about 2 to 3 hours.

The cation-reordered compound of this invention can be converted to an ordering similar to that of the conventionally ordered fully oxidized compound by heating in flowing oxygen at a temperature of at least about 800° C., preferably about 900° C. to 1000° C. for at least one day, depending on the temperature. The x-ray powder diffraction pattern of the compound which resulted when the cation-reordered material with y=0.5 was heated at 900° C. in flowing oxygen for 2.5 days, shown in Table III hereof, displays a clear (111) and a weak (333) reflection as does the diffraction pattern for the first precursor compound for y=0.5 shown in Table I hereof.

The novel compounds of the present invention are particularly useful for the selective production of aromatic products from $C_3$ and $C_4$ acyclic olefins. The process comprises contacting the acyclic olefin in the essential absence of oxygen and at a temperature of about 425° C. to 600° C. with the cation-reordered compound herein, preferably with y from 0.25 to 0.5, and recovering the aromatic product. The use of the compounds herein as catalysts has the advantage that substantial quantities of aromatic compounds are selectively produced relative to dimerized products. Moreover, when propylene is employed as olefin, the catalyst herein selectively produces benzene as substantially the only aromatic product, whereas bismuth oxide as catalyst produces substantial quantities of aromatic side products, which are difficult to separate from one another.

The acyclic olefins capable of being converted to higher molecular weight aromatic compounds are $C_3$–$C_4$ terminally or internally unsaturated linear or branched olefins such as, for example, propylene, 1- butene, 2-butene, isobutylene or mixtures of the same. The preferred olefins herein are propylene, which is selectively converted to benzene, and isobutylene, which is selectively converted to para-xylene.

Although the catalysis reaction hereof can be conducted in the presence of oxygen, it is desirable to keep the amount of oxygen at a minimum. It is preferred that less than about 5 volume %, more preferably less than about 1 volume % of oxygen be present. It is most preferred to carry out the catalysis reaction under substantially anaerobic conditions. The volume percents are based on the total volume of gases. In the typical process herein a feedstock containing the olefin substrate is passed through a bed containing the catalyst (the cation-reordered compound of this invention), which is preferaably unsupported. An inert diluent gas such as nitrogen, methane, helium, argon, or the like is preferably added to the feedstock containing the olefinic hydrocarbon to minimize risk of explosion and complete oxidation of the olefin. Typically, the feedstock contains at most 5% olefin with the remainder being helium gas.

A temperature of about 425° C. to 600° C. is generally required to achieve significant conversion of the olefins to aromatic products. If the temperature is increased much above 600° C., decomposition may occur so as to form by-products or degradation products and problems may arise with respect to any regeneration of catalyst. The preferred temperature range for the process herein is about 450° C. to 520° C.

The duration of the reaction is governed by such factors as, for example, the temperature, the amount and type of catalyst, and the rate at which the feedstock passes through the catalyst bed, which is preferably about 10 cc/min. to 50 cc/min. for a bed diameter of about 2 cm, but may be varied in accordance with the specific conditions employed. If the rate is too fast, of course, there will be a significant decrease in conversion of the feed, whereas if the rate is too slow, undesirable by-reactions may begin to occur.

After the reaction has proceeded for such a period of time that the catalyst has lost a significant amount of its lattice oxygen but prior to any destruction of the complex (for example, at about 450° C.-520° C. at 30 cc/min. for about 4 to 6 hours), the catalyst is preferably regenerated by reoxidation thereof with an oxidizing gas such as oxygen or air. The regeneration may take place at the reaction temperature or higher, preferably at 550° C.-600° C. The reaction can thus be conducted in a cyclic operation so that reaction occurs in one cycle and regeneration in a second cycle, or in a continuous operation wherein preferably two reactors are employed and a continuous stream of olefin flows through one reactor while the catalyst is regenerated in the second reactor. These cycles may be periodically reversed.

The aromatic product may be recovered by any suitable manner known in the art.

The invention is further described in the examples which follow. In the examples, all parts and percentages are by weight, and all temperatures are in °C., unless otherwise noted.

EXAMPLE 2

Preparation of $Ba_2La_{0.5}Bi_{1.5}O_6$

A mixture of 12.000 g $Ba(NO_3)_2$, 16.701 g $Bi(NO_3)_5\cdot H_2O$ and 1.870 g $La_2O_3$ was heated in air to 400° C. for two hours. The sample was reground and fired at 800° C. in air for one hour followed by regrinding and refiring at 800° C. for 60 hours. The resulting first precursor product was determined by x-ray diffraction to be a pseudo cubic perovskite material which could be indexed using a lattice parameter $a_o = 8.74(1)$ Å, (also written as $a_o = 8.74 \pm 0.01$ Å). Comparison with the lattice parameters for $Ba_2Bi_2O_6$ and $Ba_2LaBiO_6$ shows that the oxygen composition for this material is specified by $Ba_2La_{0.5}Bi_{1.5}O_6$. This material was placed in an alumina boat in a Lindberg tube furnace and heated in flowing oxygen to 950° C. for 18 hours to ensure a fully oxidized starting material, which was then cooled without removal from the furnace. The gas stream was changed to a stream consisting of oxygen and air containing 100 ppm oxygen (0.0001 atm partial pressure of oxygen) flowing at 300 cm³/min. The temperature was then raised to 950° C. and maintained for 16 hours before cooling in the same atmosphere to produce a light-brown oxygen-deficient material representing the second precursor. Without removal of the material from the furnace, the atmosphere was changed to pure oxygen flowing at 300 cm³/min. and the temperature was raised to 600° C. and maintained there for 2.5 hours before cooling in flowing oxygen to room temperature. Ancillary TGA experiments showed that these conditions were sufficient to re-oxidize fully the oxygen-deficient material formed during the treatment with 100 ppm oxygen to yield the compound of this invention.

The x-ray diffraction data for the first precursor and for the cation-reordered material obtained by re-oxidation at 600° C. of the second precursor are shown in Tables I and II respectively. The data were recorded with a Philips diffractometer using CuK radiation. The x-ray diffraction data of the material obtained by heating the cation-reordered material at 900° C. in flowing oxygen for two days is shown in Table III. It can be seen from this data that the compounds represented in Tables I and III are conventionally cation-ordered materials having a (111) and (333) reflection whereas the compounds represented in Table II are cation-reordered, and do not exhibit reflections of the type (111) and (333).

TABLE I

X-Ray Powder Diffraction Data for $Ba_2La_yBi_{2-y}O_6$, Conventional Preparation

| hkl | y = 0.25 $a_o = 8.722(5)$ Å Intensity | d-spacing (Å) | y = 0.50 $a_o$ 8.737(5) Å Intensity | d-spacing (Å) | y = 0.67 $a_o$ 8.747(5) Å Intensity | d-spacing (Å) |
|---|---|---|---|---|---|---|
| 111 | w | 5.036 | w | 5.044 | w | 5.050 |
| 200 | m | 4.361 | m | 4.369 | m⁻ | 4.374 |
| 220 | s++ | 3.084 | s++ | 3.089 | s++ | 3.093 |
| 311 | w | 2.630 | w | 2.634 | w | 2.637 |
| 400 | s | 2.181 | s | 2.184 | s | 2.187 |
| 331 | N.O. | | w⁻ | 2.004 | N.O. | |
| 420 | w+ | 1.950 | w+ | 1.954 | w+ | 1.956 |
| 422 | s+ | 1.780 | s+ | 1.783 | s+ | 1.785 |
| 333 | N.O. | | w⁻ | 1.681 | w | 1.683 |
| 440 | m+ | 1.542 | m | 1.544 | m | 1.546 |
| 531 | N.O. | | w⁻ | 1.477 | N.O. | |
| 442,600 | w | 1.454 | w | 1.456 | w⁻ | 1.458 |
| 620 | m+ | 1.379 | m | 1.381 | m | 1.383 |
| 622 | w⁻ | 1.315 | N.O | | N.O. | |
| 444 | w+ | 1.259 | w+ | 1.261 | w+ | 1.263 |
| 640 | w⁻ | 1.210 | w⁻ | 1.212 | N.O. | |
| 642 | m | 1.166 | m+ | 1.168 | m | 1.169 |

NOTE:
w = weak; m = medium, s = strong, N.O. = not observed.

TABLE II

X-Ray Powder Diffraction Data for $Ba_2La_yBi_{2-y}O_6$, Cation Reordered

| | y = 0.25 $a_o$ 8.722(5) Å | | y = 0.50 $a_o$ 8.755(5) Å | | y = 0.67 $a_o$ 8.77(5) Å | |
|---|---|---|---|---|---|---|
| hkl | Intensity | d-spacing (Å) | Intensity | d-spacing (Å) | Intensity | d-spacing (Å) |
| 111 | N.O. | | N.O. | | N.O. | |
| 200 | m | 4.361 | m+ | 4.378 | m | 4.387 |
| 220 | s++ | 3.084 | s++ | 3.095 | s++ | 3.102 |
| 311 | w− | 2.360 | w | 2.640 | w− | 2.646 |
| | | | w− | 2.350 | | |
| 400 | s | 2.181 | s | 2.189 | s | 2.194 |
| | | | w | 2.032 | | |
| 331 | N.O. | | N.O. | | N.O. | |
| 420 | w+ | 1.950 | w+ | 1.958 | w+ | 1.962 |
| 422 | s+ | 1.780 | s+ | 1.787 | s+ | 1.791 |
| 333 | N.O. | | N.O. | | N.O. | |
| 440 | m+ | 1.542 | m+ | 1.548 | m | 1.551 |
| 531 | N.O. | | N.O. | | N.O. | |
| 442,600 | w | 1.454 | w | 1.459 | w | 1.463 |
| 620 | m+ | 1.379 | m+ | 1.384 | m | 1.387 |
| 622 | w− | 1.315 | w− | 1.320 | N.O. | |
| 444 | w+ | 1.259 | w+ | 1.264 | w+ | 1.267 |
| 640 | w− | 1.210 | w− | 1.214 | N.O. | |
| 642 | m | 1.166 | m+ | 1.170 | m | 1.173 |

NOTE:
w = weak; m = medium, s = strong, N.O. = not observed.

TABLE III

X-ray Powder Diffraction Data for $Ba_2La_{.5}Bi_{1.5}O_6$ After Cation-Reordering Followed by 900° C., $O_2$, 2½ days

| hkl | Intensity | d*-spacing (Å) |
|---|---|---|
| 111 | w | 5.044 |
| 200 | m | 4.369 |
| 220 | s++ | 3.089 |
| 311 | w | 2.634 |
| 400 | s | 2.184 |
| 331 | w− | 2.004 |
| 420 | w+ | 1.954 |
| 422 | s+ | 1.783 |
| 333 | w− | 1.681 |
| 440 | m+ | 1.544 |
| 531 | N.O. | |
| 442,600 | w | 1.456 |
| 620 | m+ | 1.381 |
| 444 | w+ | 1.261 |
| 640 | w− | 1.212 |
| 642 | m+ | 1.168 |

NOTE:
w = weak, m = medium, s = strong, N.O. = not observed.
*The pseudo-cubic lattice constant for this material, $a_o$ = 8.737(5) Å, is equivalent to that for the conventional preparation of the same composition (See Table I).

EXAMPLE 2

Preparation of $Ba_2La_{0.25}Bi_{1.75}O_6$

A mixture of 10.454 g of $Ba(NO_3)_2$, 16.974 g of $Bi(NO_3)_3.5H_2O$ and 0.815 g of $La_2O_3$ was heated as described in Example 1 except that the final firing in air was done at 900° C. instead of 800° C. The resulting first precursor product was determined by x-ray diffraction to be a pseudo-cubic perovskite material which could be indexed with a lattice parameter $a_o$=8.72(1) Å. Comparison with the lattice parameters for $Ba_2Bi_2O_6$ ($a_o$=8.71(1) Å) and for $Ba_2LaBiO_6$ ($a_o$=8.77(1) Å) shows that the oxygen composition of this material is given by $Ba_2La_{0.25}Bi_{1.75}O_6$. This material was placed in an alumina boat in a Lindberg tube furnace and heated at 920° C. for 14 hours in a gas stream consisting of oxygen and argon containing 1000 ppm oxygen (0.001 atm partial pressure of oxygen) flowing at 300 cm$^3$/min. before cooling in the same atmosphere to produce an oxygen-deficient material, light brown in color, representing the second precursor. Ancillary TGA experiments showed that these conditions were sufficient to form $Ba_2La_{0.25}Bi_{1.75}O_5$. Without removal of the material from the furnace, the atmosphere was changed to pure oxygen flowing at 300 cm$^3$/min. and the temperature was raised to 600° C. and maintained there for 2 hours before cooling in flowing oxygen to room temperature. Ancillary TGA experiments showed that these conditions were sufficient to fully reoxidize the oxygen-deficient material formed during the treatment with 1000 ppm oxygen to yield the compound of the invention.

The x-ray diffraction data for the first precursor and for the cation-reordered material obtained by re-oxidation at 600° C. of the second precursor are shown in Tables I and II, respectively. It can be seen that the (111) and (333) reflections are absent for the compound of composition $Ba_2La_{0.25}Bi_{1.75}O_6$ in Table II, indicating that this compound has been cation-reordered.

EXAMPLE 3

Preparation of $Ba_2La_{0.67}Bi_{1.33}O_6$

A mixture of 10.454 g of $Ba(NO_3)_2$, 2.183 g of $La_2O_3$ and 12.9 g of $Bi(NO_3)_3.5H_2O$ was heated as described in Example 1 except that the final heating was done at 900° C. instead of 800° C. The resulting first precursor product was determined by x-ray diffraction to be a pseudo-cubic perovskite with lattice parameter $a_o$=8.75(1) Å. Comparison with the lattice parameters for $Ba_2Bi_2O_6$ ($a_o$=8.71 Å) and $Ba_2BiLaO_6$ ($a_o$=8.77 Å) shows that the oxygen composition for this material is given by $Ba_2La_{0.67}Bi_{1.33}O_6$. A 6 g sample of this material was placed in an alumina boat in a Lindberg tube furnace and heated in flowing oxygen to 900° C. for 2 hours to ensure a fully oxidized starting material which was cooled without removal from the furnace. The gas stream was charged to a stream of purified argon (0.000002 atm partial pressure of oxygen) flowing at 300 cm$^3$/min. The temperature was raised to 950° C. and maintained there for 16 hours and then increased to 1000° C. for an additional 24 hours before cooling in the same atmosphere to obtain a bright yellow oxygen-deficient material representing the second precursor. Ancillary TGA experiments showed that these conditions were sufficient to form $Ba_2La_{0.67}Bi_{1.33}O_5$. Without removal of the sample from the furnace the atmosphere was changed to pure oxygen flowing at 300 cm$^3$/min. and the temperature was raised to 600° C. and maintained for 2 hours before cooling in the same atmosphere to room temperature. Ancillary TGA experiments showed that these conditions were sufficient to fully reoxidize the oxygen deficient material formed in the previous step to yield the compound of the invention.

The x-ray diffraction pattern for the first precursor and for the cation-reordered material obtained by reoxidation at 600° C. of the second precursor are shown in Tables I and II. It can be seen that the (111) and (333) reflections are absent for the compound of composition $Ba_2La_{0.67}Bi_{1.33}O_6$ in Table II indicating that this compound has been cation-reordered.

EXAMPLE 4

Selective Production of Benzene

In four separate experiments, each of the four materials A–D, having the composition $Ba_2La_{0.5}Bi_{1.5}O_6$, was singly deposited in an amount of 3 grams in a quartz upflow reactor with a 0.75 inch (1.9 cm) diameter. Material A was the final product of Example 1. Material B was the material resulting when Material A was heated in flowing oxygen at 900° C. for 2.5 days. Material C was the first product of Example 1, i.e., the material obtained on successive regrindings and refirings to 800° C. of a mixture of $Ba(NO_3)_2$, $Bi(NO_3)_3.5H_2O$ and $La_2O_3$ heated in air. Material D was obtained by heating Material C in flowing oxygen at 950° C. for one day followed by 3.5 days at 900° C. Thus, Material A is a cation-reordered material of this invention and Material B is obtained by high temperature treatment of Material A. Materials C and D represent conventionally ordered materials as a comparison.

A feedstream consisting of about 5% propylene and 95% helium flowing at a rate of 30 cc min$^{-1}$ was passed through the reactor which was heated to a temperature of 475° C. After about $2\frac{1}{4}$ hours of reaction at 475° C. the temperature was increased to 510° C. and the reactions proceeded at the higher temperature to yield a total reaction time of six hours. Each reaction was monitored by injecting, at regular intervals, a sample of each product reaction mixture into a gas chromatograph. The identity and relative amounts of each product were thereby determined.

Figure 2:
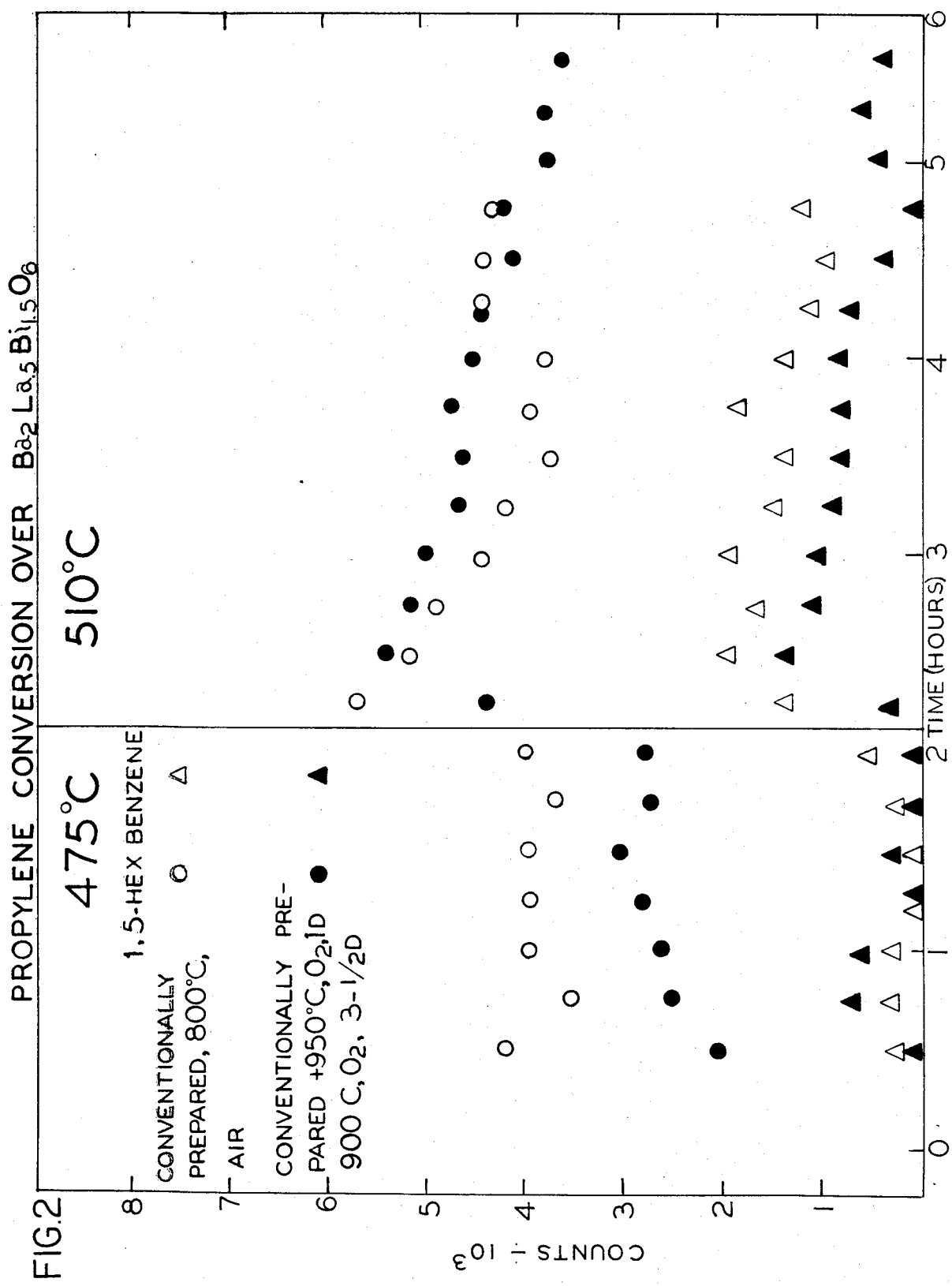
FIG. 2 is a graphical representation showing the relative amounts of 1,5 hexadiene and benzene produced from propylene (5% in helium) as a function of time at two different temperatures, 475° C. and 510° C., by use of two conventional cation ordered materials (C and D) both of which are represented by the formula $Ba_2La_{0.5}Bi_{1.5}O_6$ wherein material C is a first precursor compound as herein described and material D is the product of heating a sample of material C in flowing oxygen at 950° C. for one day followed by heating at 900° C. for 3.5 days.

The results obtained for Materials A and B, on the one hand, and Materials C and D, on the other hand, are shown in FIGS. 1 and 2, respectively, which represents plots of the relative amounts of 1,5-hexadiene and benzene formed as a function of time. All four materials showed low production of carbon oxides, low benzene make, and comparable production of the 1,5-hexadiene dimer which was the dominant product during the initial reaction at 475° C. Materials A and B did, however, show a small early build-up of benzene which was much less pronounced with Materials C and D at 475° C. The most dramatic differences among the four materials occurred upon increasing the reaction temperature from 475° to 510° C. Both Materials A and B, representing the cation-reordered material and its high temperature oxygen treated counterpart, respectively, showed a substantial build-up of benzene production with an accompanying rapid decrease in the production of the dimer. Thus, the selectivity for conversion of propylene to benzene at 510° C. was nearly 100% after an initial induction period of about 1.5 hours and 3 hours for Materials A and B, respectively. On comparing the results in FIG. 1 with those in FIG. 2, it can be seen that the steady-state production of benzene by the materials which have undergone cation reordering (of FIG. 1) is greater by a factor of six to eight than the production of benzene by the conventionally ordered materials (of FIG. 2), which were tested under identical conditions. Moreover, when a perovskite of the composition $Ba_2LaBiO_6$, prepared by mixing appropriate molar amounts of barium nitrate, bismuth nitrate pentahydrate, and lanthanum oxide, heating the mixture to 400° C. for 2 to 3 hours then cooling and grinding in air and reheating to 800° C. in air for 60 hours in a furnace with an intermediate regrind, was tested under identical conditions for conversion of propylene to benzene, it was found to have a lower conversion rate than Materials A and B by about a factor of one-half, even though the latter materials have a lower La to Bi ratio.

X-ray diffraction analysis of the solid reaction products obtained after the catalytic reactions were completed showed that for Materials A and B significant quantities of the oxygen-deficient material $Ba_2La_{0.5}Bi_{1.5}O_5$ were present, while for comparative Materials C and D, which exhibited much lower conversion rates, the dominant phase was the fully oxidized material $Ba_2La_{0.5}Bi_{1.5}O_6$ and little if any $Ba_2La_{0.5}Bi_{1.5}O_5$ was present.

In an additional experiment, the solid product material produced by reacting Material A with propylene was removed from the reactor and was regenerated by reoxidation at 600° C. in flowing oxygen. Using a mixture of 5% propylene in helium and conditions identical to those described above, the results showed that the regenerated material produced approximately equal amounts of the 1,5-hexadiene and benzene at 475° C. at a level very comparable to that obtained using Material A. When the temperature was increased to 500° C., the benzene production rapidly increased to about 150% of the maximum level shown in FIG. 1. As observed with Material A the production of 1,5-hexadiene rapidly decreased, so that after two hours at 510° C. the regenerated material effected essentially 100% conversion of propylene to benzene with a slow decrease in benzene production as time progressed. The results thus show that the loss in activity due to depletion of lattice oxygen may be avoided by treatment of the oxygen-deficient cation-reordered material with oxygen.

EXAMPLE 5

Selective Production of Benzene from $Ba_2La_{0.25}Bi_{1.75}O_6$

In two separate experiments, each of two materials E and F, having the composition $Ba_2La_{0.25}Bi_{1.75}O_6$, was separately deposited in the amount of 3 grams in a quartz upflow reactor with a 0.75 inch (1.9 cm) diameter. Material E was cation reordered while Material F was conventionally ordered, each having each prepared as described in Example 2 where Material E is the final product and Material F is the first precursor product of Example 2.

A feedstream consisting of about 5% propylene and 95% helium flowing at a rate of 30 cc min$^{-1}$ was passed through the reactor which was heated to a temperature of 475° C. After about $2\frac{1}{4}$ hours of reaction at 475° C., the temperature was increased to 500° C., and the reactions proceeded at the higher temperature to yield a total reaction time of seven hours. Each reaction was monitored by injecting, at regular intervals, a sample of each product reaction mixture into a gas chromatograph. The identity and relative amounts of each product were thereby determined.

Figure 3:
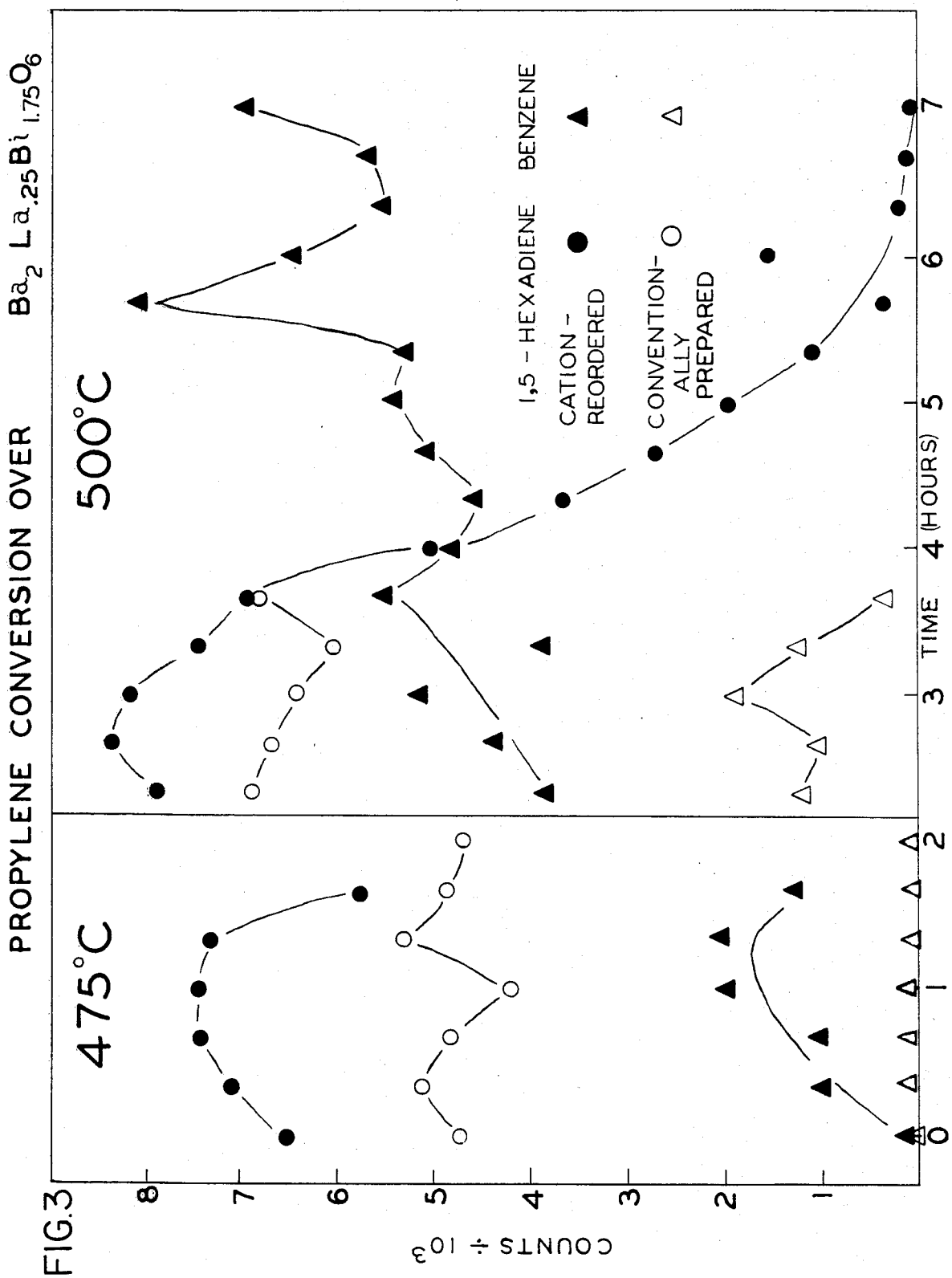
FIG. 3 is a graphical representation showing the relative amounts of 1,5 hexadiene and benzene produced from propylene (5% in helium) as a function of time at temperatures of 475° C. and 500° C. by use of two materials (E and F), both of which are represented by the formula $Ba_2La_{0.25}Bi_{1.75}O_6$ wherein material E is cation re-ordered and F is conventionally cation ordered.

The results obtained for Materials E and F are shown in FIG. 3 which represents plots of the relative amounts of 1,5-hexadiene and benzene formed as a function of time. Both materials showed low production of carbon oxides, low benzene make, and comparable production of the 1,5-hexadiene dimer which was the dominant product during the initial reaction at 475° C. At 475° C., material E did show a small early build-up of benzene which was absent for Material F. A dramatic difference between these two materials occurred upon increasing the reaction temperature from 475° to 500° C. Material E, representing the cation-reordered material, showed a substantial build-up of benzene production with an accompanying rapid decrease in the production of the dimer, while Material F, representing the conventionally ordered material, continued to produce the dimer as the dominant product. For the cation-reordered Material E, the selectivity for conversion of propylene to benzene at 500° C. was nearly 100% after an initial induction period of about four hours. Comparing the results for Materials E and F given in FIG. 3, it is clear that the cation reordered process increases the overall propylene conversion rate and dramatically improves selectivity toward the aromatic product as the reaction temperature is increased from 475° C. to 500° C.

EXAMPLE 6

Selective Production of Benzene from $Ba_2La_{0.67}Bi_{1.33}O_6$

In two separate experiments, each of two Materials G and H, having the composition $Ba_2La_{0.67}Bi_{1.33}O_6$, was separately deposited in the amount of 3 grams in a quartz upflow reactor with a 0.75 inch (1.9 cm) diameter. Material G was cation reordered, while Material H was conventionally ordered each having been prepared as described in Example 3 where Material G is the final product and Material H is the first precursor product of Example 3.

A feedstream consisting of about 5% propylene and 95% helium flowing at a rate of 30 cm min$^{-1}$ was passed through the reactor which was heated to a temperature of 475° C. After about 1¾ hours of reaction at 475° C., the temperature was increased to 500° C. and the reactions proceeded at the higher temperature to yield a total reaction time of 4¼ hours. Each reaction was monitored by injecting, at regular intervals, a sample of each product reaction mixture into a gas chromatograph. The identity and relative amounts of each product were thereby determined.

Figure 4:
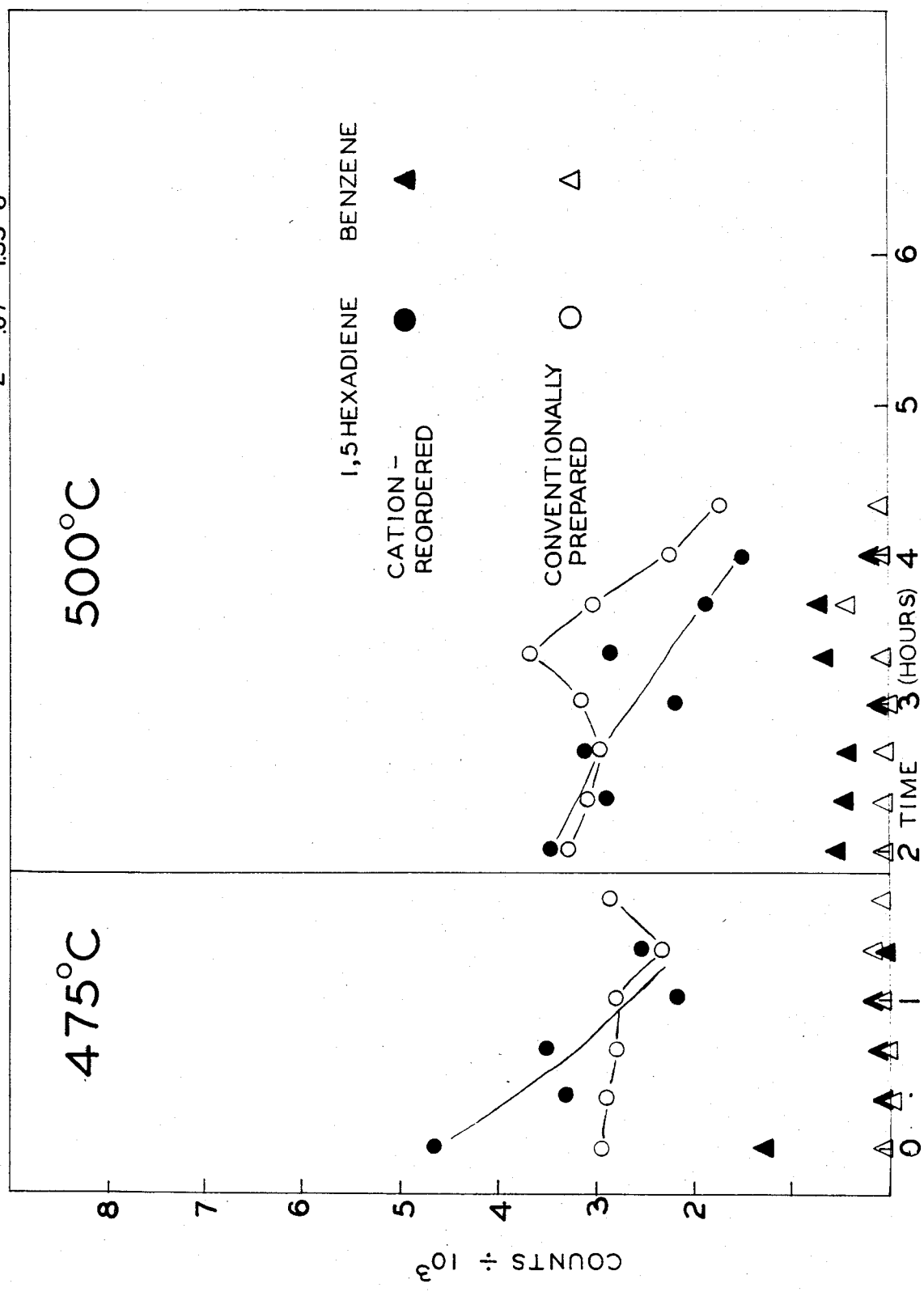
FIG. 4 is a graphical representation showing the relative amounts of 1,5 hexadiene and benzene produced from propylene (5% in helium) as a function of time at temperatures of 475° C. and 500° C. by use of two materials (G and H), both of which are represented by the formula $Ba_2La_{0.67}Bi_{1.33}O_6$ wherein material G is cation-reordered and H is conventionally cation ordered.

The results obtained for Materials G and H are shown in FIG. 4 which represents plots of the relative amounts of 1,5-hexadiene and benzene formed as a function of time. Both materials showed low production of carbon oxides, low benzene make, and comparable production of the 1,5-hexadiene dimer which was essentially the only product during the initial reaction at 475° C. Material G showed a slight build-up of benzene as the temperature was increased to 500° C., while Material H showed essentially no benzene yield even at 500° C. Both materials showed a gradual decline over several hours in production of the dimer as the reactor temperature was held at 500° C.

In summary, the present invention is seen to provide a class of fully oxidized, cation-reordered, bismuth- and lanthanum-containing compounds having a perovskite-type structure and a process for the preparation thereof. Also provided is a process for selectively producing aromatic products from $C_3$–$C_4$ acyclic olefins using the class of compounds herein.

What is claimed is:

1. A cation-reordered, bismuth-containing compound having a perovskite-type structure of the formula:

$$Ba_2La_yBi_{2-y}O_6$$

wherein y is greater than 0 but less than 1, the compound being further characterized by having the x-ray powder diffraction pattern indicated in Table II.

2. A compound according to claim 1 which is prepared by heating a compound having a perovskite-type structure of the formula:

$$Ba_2La_yBi_{2-y}O_{6-x}$$

wherein y and x are greater than 0 but less than 1, at a temperature no greater than about 600° C. in flowing oxygen.

3. A compound according to claim 1 wherein y is from 0.25 to 0.75.

4. A compound according to claim 1 wherein y is 0.5.

5. A process for preparing a cation-reordered, bismuth-containing compound having a perovskite-type structure of the formula:

$$Ba_2La_yBi_{2-y}O_6$$

wherein y is greater than 0 but less than 1, the compound having the x-ray powder diffraction pattern indicated in Table II, which process comprises:

(a) heating a first precursor compound of the formula:

$$Ba_2La_yBi_{2-y}O_6$$

wherein y is defined above and having the x-ray diffraction pattern given in Table I, in the presence of an effective amount of oxygen at a temperature of at least about 600° C., depending on the particular precursor compound and the amount of oxygen present, for a sufficient period of time to produce a second precursor compound which is oxygen deficient and has a perovskite-type structure of the formula:

$$Ba_2La_yBi_{2-y}O_{6-x}$$

where y is defined above and x is greater than 0 but no greater than 1; and (b) heating the second precursor compound at a temperature no greater than about 650° C. in flowing oxygen for a sufficient period of time to reoxidize the second precursor compound.

6. A process according to claim 5 wherein y is 0.25 to 0.75.

7. A process according to claim 5 wherein y is 0.5.

8. A process according to claim 5 wherein the first precursor compound is prepared from a mixture of $Ba(NO_3)_2$, $Bi(NO_3)_3 \cdot 5H_2O$ and $La_2O_3$.

9. A process according to claim 8 wherein the mixture is heated in air to about 800° C.

10. A process according to claim 5 wherein the first precursor compound is heated at from about 600° C. to 1000° C., depending on the particular precursor compound and the amount of oxygen present.

11. A process according to claim 5 wherein the first precursor compound is heated at from about 800° C. to 1000° C., depending on the particular precursor compound and the amount of oxygen present.

12. A process according to claim 5 wherein the amount of oxygen present is sufficient to yield an oxygen partial pressure of between about 0.001 and 0.000001 atm.

13. A process according to claim 5 wherein the first precursor compound is heated at an oxygen partial pressure of between about 0.001 and 0.00001 atm and at a temperature of 900° C. to 1000° C., depending on the oxygen partial pressure.

14. A process according to claim 5 wherein the first precursor compound is heated at 950° C. at an oxygen partial pressure of 0.0001 atm for at least 8 hours and y is 0.5.

15. A process according to claim 5 wherein the second precursor compound is heated at a temperature of about 250° to 650° C.

16. A process according to claim 14 wherein the second precursor compound is heated at a temperature of about 600° C. for at least 2.5 hours.

* * * * *